US009179920B2

(12) United States Patent
Ren

(10) Patent No.: US 9,179,920 B2
(45) Date of Patent: *Nov. 10, 2015

(54) OCCLUSION DEVICE AND ASSOCIATED DEPLOYMENT METHOD

(71) Applicant: AGA Medical Corporation, Plymouth, MN (US)

(72) Inventor: Brooke Ren, Maple Grove, MN (US)

(73) Assignee: AGA MEDICAL CORPORATION, Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/282,121

(22) Filed: May 20, 2014

(65) Prior Publication Data

US 2014/0257357 A1 Sep. 11, 2014

Related U.S. Application Data

(63) Continuation of application No. 13/163,313, filed on Jun. 17, 2011, now Pat. No. 8,764,787.

(51) Int. Cl.
*A61B 17/12* (2006.01)

(52) U.S. Cl.
CPC ..... *A61B 17/12122* (2013.01); *A61B 17/12172* (2013.01)

(58) Field of Classification Search
CPC ................... A61B 17/12022; A61B 17/12099; A61B 17/12109; A61B 17/12113; A61B 17/12122; A61B 17/1214; A61B 17/12145; A61B 17/12168; A61B 17/12172
USPC ........... 606/32, 157, 158, 191, 192, 193, 194, 606/195, 196, 197, 198, 199, 200, 213, 214, 606/215, 216, 217
See application file for complete search history.

(56) References Cited

U.S. PATENT DOCUMENTS

| 4,457,028 A | 7/1984 | Draenert |
| 6,375,668 B1 | 4/2002 | Gifford et al. |

(Continued)

FOREIGN PATENT DOCUMENTS

| CN | 1711978 A | 12/2005 |
| CN | 101304693 A | 11/2008 |

(Continued)

OTHER PUBLICATIONS

Dictionary.com definition of fiber as accessed Dec. 31, 2014; http://dictionary.reference.com/browse/fiber.*

(Continued)

*Primary Examiner* — Jonathan W Miles
(74) *Attorney, Agent, or Firm* — Armstrong Teasdale LLP

(57) ABSTRACT

An occlusion device for occluding a cavity defined by a body is provided, and includes first and second laterally-expandable portions each formed of a woven tubular fabric and having opposed proximal and distal ends. The first portion is insertable into the cavity so as to be substantially disposed therein upon lateral expansion thereof. A connective element tethers the distal end of the first portion and the second portion, and is cooperable therewith to form a collapsible assembly extending along an insertion axis. Retention members, operably engaged with each of the first and second portions and spaced apart about a laterally outward surface thereof, are adapted to engage the body, after insertion of the collapsed assembly, second portion-first, into the cavity, and subsequent lateral expansion of the first and second portions, so as to retain the assembly substantially within the cavity. An associated deployment method is also provided.

20 Claims, 5 Drawing Sheets

(56) References Cited

U.S. PATENT DOCUMENTS

Figure 1:
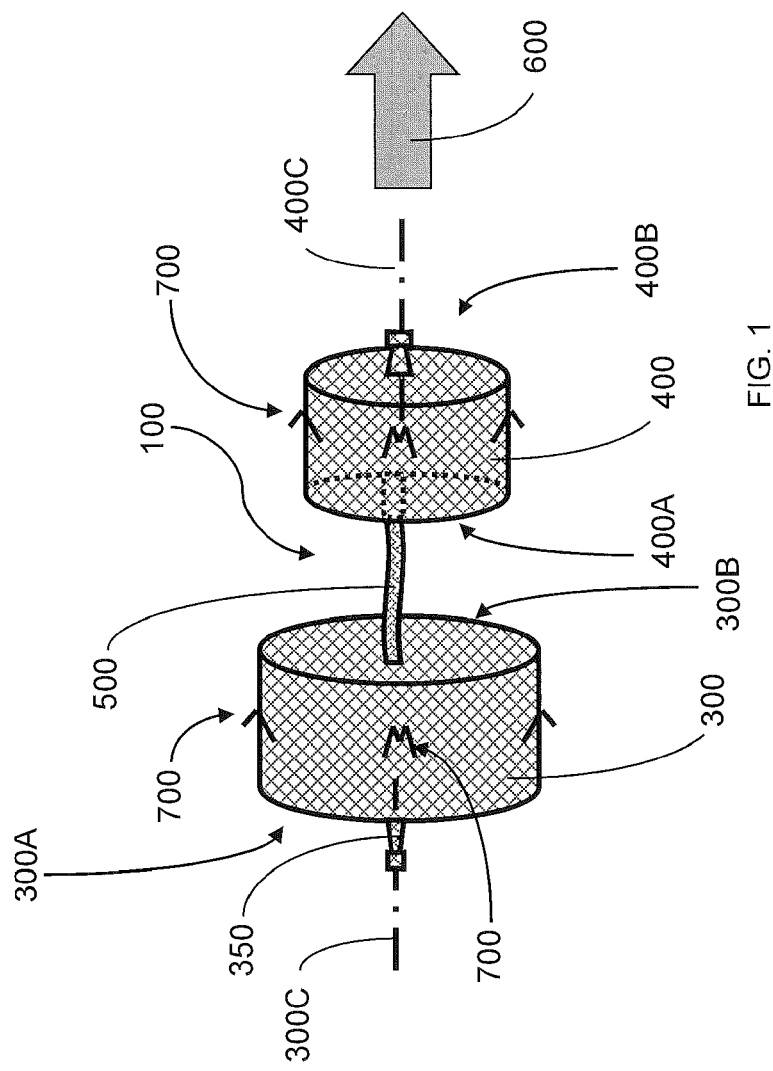

| | | |
|---|---|---|
| 6,652,556 B1 | 11/2003 | VanTassel et al. |
| 2002/0143349 A1 | 10/2002 | Gifford, III et al. |
| 2002/0173819 A1 | 11/2002 | Leeflang et al. |
| 2003/0220667 A1 | 11/2003 | van der Burg et al. |
| 2004/0172051 A1 | 9/2004 | Ravikumar |
| 2006/0241690 A1 | 10/2006 | Amplatz et al. |
| 2006/0247680 A1 | 11/2006 | Amplatz et al. |
| 2007/0265656 A1 | 11/2007 | Amplatz et al. |
| 2009/0018562 A1 | 1/2009 | Amplatz et al. |
| 2009/0025820 A1 | 1/2009 | Adams |
| 2009/0062841 A1 | 3/2009 | Amplatz et al. |
| 2009/0099647 A1 | 4/2009 | Glimsdale et al. |
| 2009/0112251 A1 | 4/2009 | Qian et al. |
| 2009/0171386 A1 | 7/2009 | Amplatz et al. |
| 2009/0192588 A1* | 7/2009 | Shin et al. .................. 623/1.15 |
| 2010/0030321 A1 | 2/2010 | Mach |
| 2010/0076463 A1 | 3/2010 | Mavani et al. |
| 2010/0211046 A1 | 8/2010 | Adams et al. |
| 2010/0228184 A1 | 9/2010 | Mavani et al. |

FOREIGN PATENT DOCUMENTS

| | | |
|---|---|---|
| WO | 2005099365 A2 | 10/2005 |
| WO | 2010028300 A1 | 3/2010 |

OTHER PUBLICATIONS

International Search Report and Written Opinion from International Patent Application No. PCT/US2012/041203, mailed Nov. 2, 2012.
Notification Concerning Transmittal of International Preliminary Report on Patentability for Application No. PCT/US2012/041203 dated Jan. 3, 2014; 10 pages.

* cited by examiner

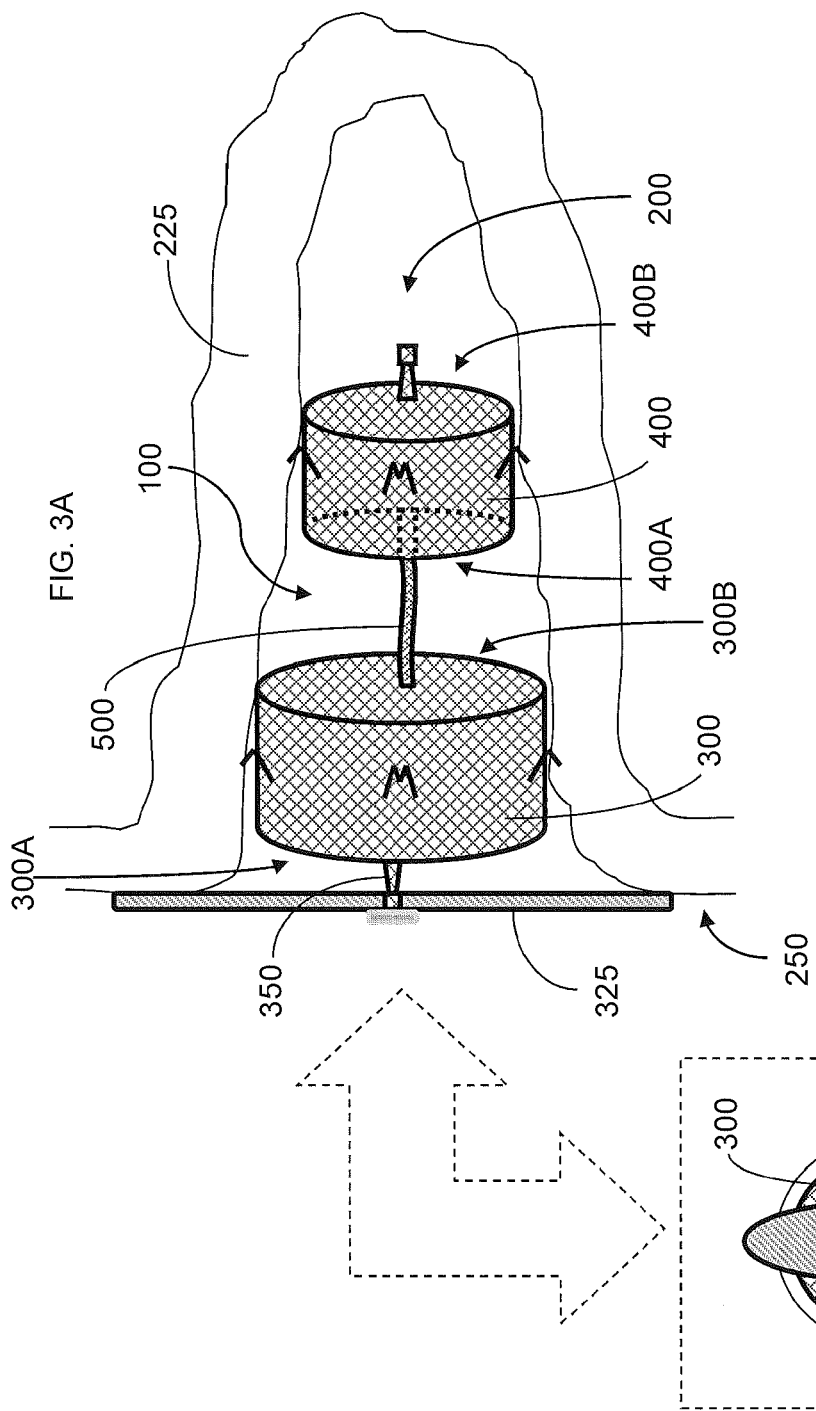

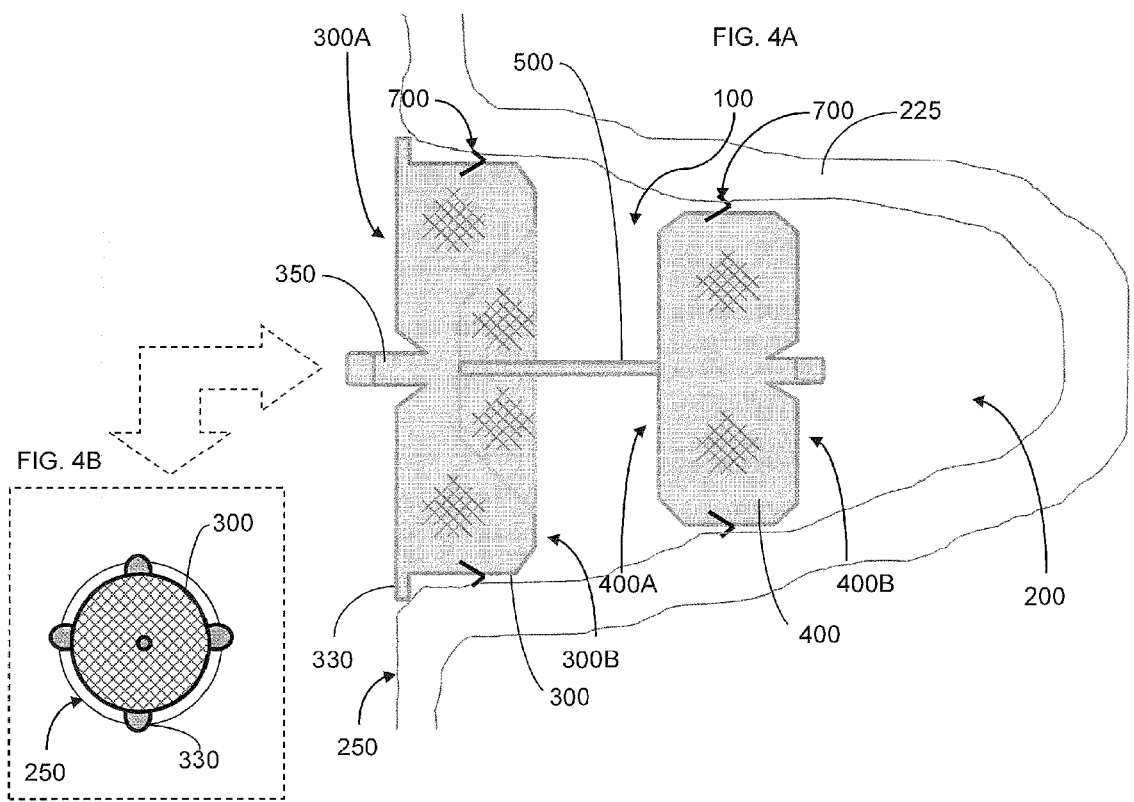

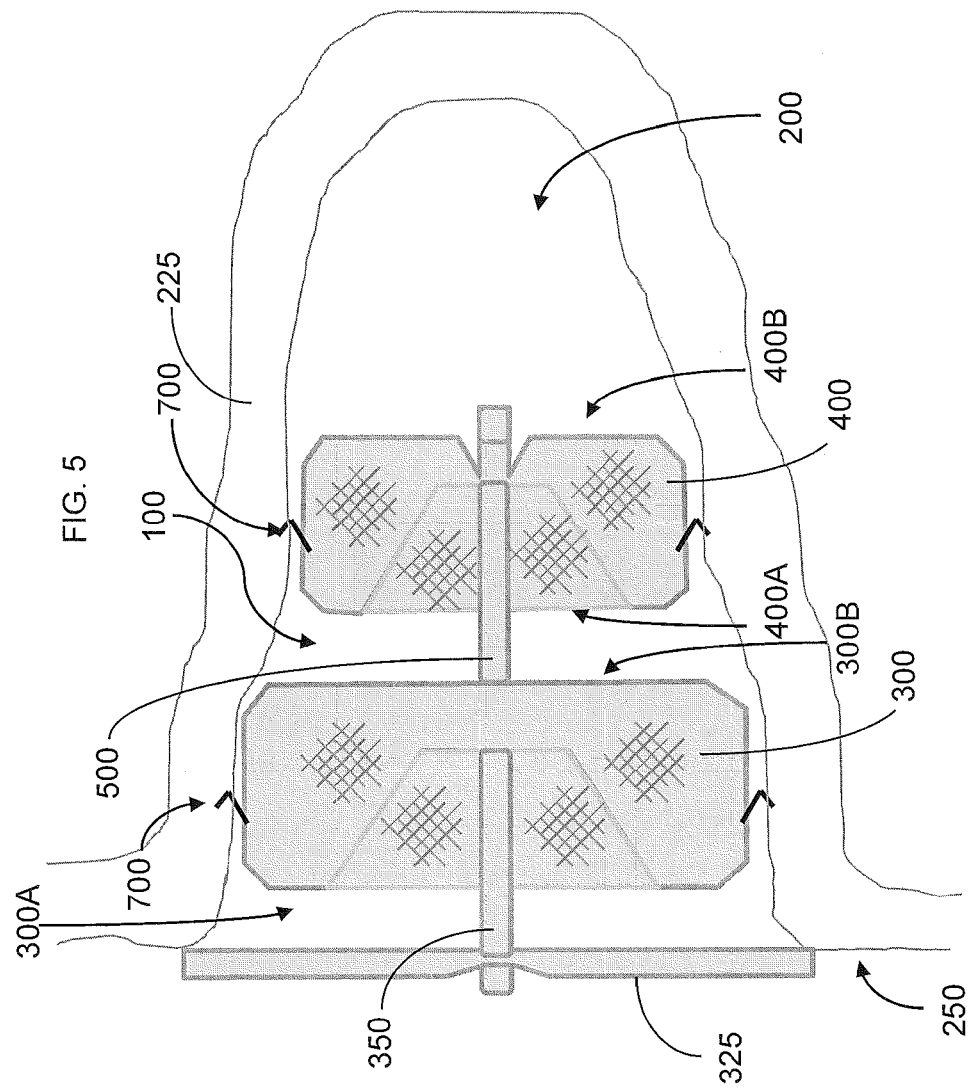

OCCLUSION DEVICE AND ASSOCIATED DEPLOYMENT METHOD

CROSS-REFERENCE TO RELATED APPLICATIONS

This application is a continuation of U.S. Ser. No. 13/163,313, filed on Jun. 17, 2011, which is incorporated herein by reference in its entirety.

BACKGROUND OF THE DISCLOSURE

1. Field of the Disclosure

Aspects of the present disclosure are directed to implantable medical devices, more particularly to implantable medical devices configured to occlude vessels, cavities, appendages, or the like, within a body, and deployment methods associated therewith.

2. Description of Related Art

A variety of devices and/or techniques, along with materials for and methods of manufacturing such devices, have been developed to occlude a vessel or an opening in an organ (e.g., heart) of a patient.

Such devices, however, may not be particularly suited to address specific physiological conditions such as, e.g., occlusion of the left atrial appendage (LAA), in order to reduce the risk of embolisms when the patient is undergoing atrial fibrillation. During atrial fibrillation, the left atrial appendage may be a significant source of the undesirable formation of thrombus-embolis. Also, occlusion of the left atrial appendage by surgical techniques may not always be possible and/or advisable. Further, some such devices applied to occlude the left atrial appendage may sometimes be at risk of being undesirably expelled from the left atrial appendage due to, e.g., forces generated by atrial fibrillation. In addition, some such devices may be configured so as to undesirably prevent some subsequent alternate treatments of the condition such as, e.g., ablation therapy for atrial fibrillation.

As such, there exists a need for an occlusion device and associated deployment method capable of addressing the above-noted and other factors involved in therapies for atrial fibrillation of the left atrial appendage and/or other vessels, cavities, appendages, or the like, within the body.

BRIEF SUMMARY OF THE DISCLOSURE

The above and other needs are met by aspects of the present disclosure which, in one aspect, provides an occlusion device adapted to be received within and to occlude a cavity defined by a body, wherein the body comprises tissue forming a rim defining an opening extending into the cavity. Such an occlusion device comprises a first laterally-expandable portion formed of at least one metal strand woven into at least one layer of a tubular fabric, and having opposed proximal and distal ends. The first portion is configured to be insertable into the cavity through the opening so as to be substantially disposed within the cavity upon lateral expansion thereof. A second laterally-expandable portion is formed of at least one metal strand woven into at least one layer of a tubular fabric, wherein the second portion has opposed proximal and distal ends and is configured to be insertable into the cavity distally to the first portion. A connective element is operably engaged with and tethers the distal end of the first portion to the second portion, and is cooperable therewith to form a collapsible assembly extending along an insertion axis. A plurality of retention members may be operably engaged with at least one of the first and second portions, and the retention members may be spaced apart about a laterally outward surface thereof. The retention members may be adapted to engage the body, upon insertion of the collapsible assembly, in a collapsed state and with the second portion first inserted distally to the first portion, into the cavity along the insertion axis, and upon subsequent lateral expansion of the first and second portions, so as to retain the assembly within the cavity.

Another aspect of the disclosure is directed to a method of deploying an occlusion device into and to occlude a cavity defined by a body, wherein the body comprises tissue forming a rim defining an opening extending into the cavity. Such a method comprises inserting a collapsed occlusion assembly along an insertion axis thereof into the cavity through the opening, wherein the occlusion assembly has a leading end and a trailing end. Such an assembly includes a first laterally-expandable portion formed of at least one metal strand woven into at least one layer of a tubular fabric and having opposed proximal and distal ends, wherein the first portion is disposed toward the trailing end. A second laterally-expandable portion is formed of at least one metal strand woven into at least one layer of a tubular fabric and has opposed proximal and distal ends, wherein the second portion is disposed toward the leading end. A connective element is operably engaged with and tethers the distal end of the first portion to the second portion. A plurality of retention members may be operably engaged with each of the first and second portions, and the retention members may be spaced apart about a laterally outward surface thereof. The assembly is then actuated, wherein the first and second portions thereof are responsive to the actuation so as to laterally expand to engage the body defining the cavity, such that the retention members engage the body to retain the assembly substantially within the cavity.

Aspects of the present disclosure thus address the identified needs and provide other advantages as otherwise detailed herein.

BRIEF DESCRIPTION OF THE SEVERAL VIEWS OF THE DRAWING(S)

Figure 2:
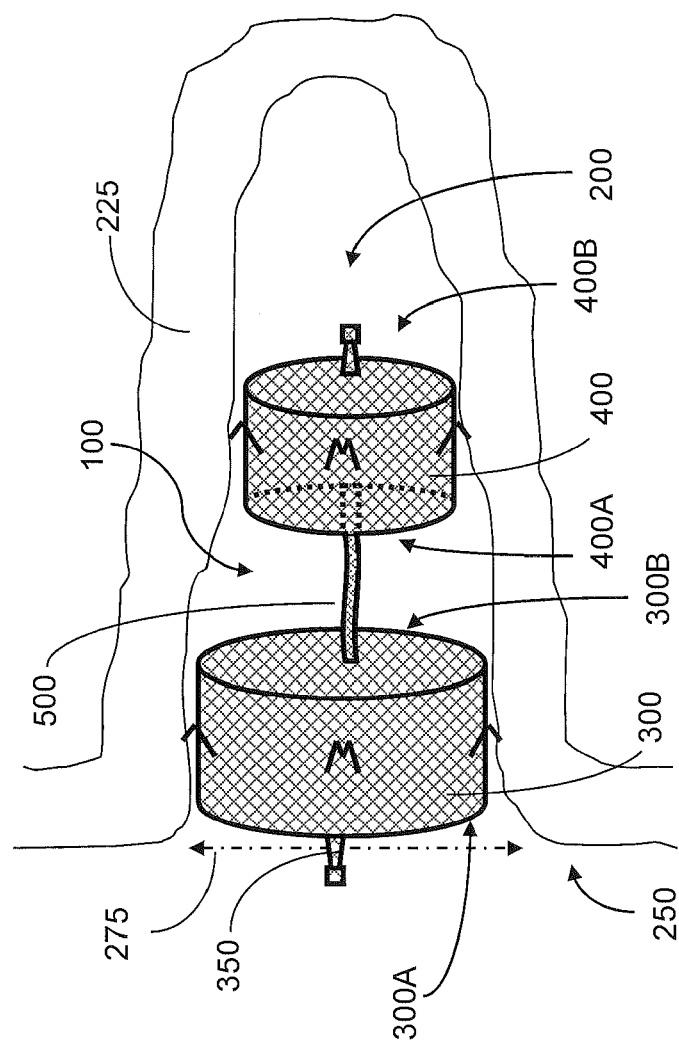

Having thus described the disclosure in general terms, reference will now be made to the accompanying drawings, which are not necessarily drawn to scale, and wherein:

FIG. 1 schematically illustrates an occlusion device, according to one aspect of the present disclosure;

FIG. 2 schematically illustrates an occlusion device, according to one aspect of the present disclosure, inserted into and deployed in an exemplary bodily cavity;

FIGS. 3A and 3B schematically illustrate side and front elevations, respectively, of an occlusion device according to another aspect of the present disclosure, inserted into and deployed in an exemplary bodily cavity;

FIGS. 4A and 4B schematically illustrate cross-sectional and front elevations, respectively, of an occlusion device according to another aspect of the present disclosure, inserted into and deployed in an exemplary bodily cavity; and FIG. 5 schematically illustrates a cross-sectional elevation of an occlusion device according to another aspect of the present disclosure, inserted into and deployed in an exemplary bodily cavity.

DETAILED DESCRIPTION OF THE DISCLOSURE

The present disclosure now will be described more fully hereinafter with reference to the accompanying drawings, in which some, but not all aspects of the disclosure are shown.

Indeed, the disclosure may be embodied in many different forms and should not be construed as being limited to the aspects set forth herein; rather, these aspects are provided so that this disclosure will satisfy applicable legal requirements. Like numbers refer to like elements throughout.

Aspects of the present disclosure provide a medical device for use in treating a target site within the body, such as occluding various vascular abnormalities, which may include, for example, occluding a Left Atrial Appendage (LAA), an Arterial Venous Malformation (AVM), a Patent Ductus Arteriosus (PDA), or the like. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a congenital defect, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, a septum, or the like.

According to one aspect of the present disclosure for forming a medical device, the device includes one or more layers of braided fabric, wherein each layer may be formed of at least one wire strand woven into a tubular fabric, or a plurality of filaments having a predetermined relative orientation with respect to one another. Moreover, the device may comprise a plurality of layers of occluding material such that the device may be a variety of occluding materials capable of at least partially inhibiting blood flow therethrough in order to facilitate the formation of thrombus and epithelialization around the device.

Although the term "strand" is discussed herein, "strand" is not meant to be limiting, as it is understood the fabric may comprise one or more wires, cords, fibers, yarns, filaments, cables, threads, or the like, such that such terms may be used interchangeably. As used herein the term "proximal" shall mean closest to the operator (less into the body) and "distal" shall mean furthest from the operator (further into the body). In positioning of the medical device from a downstream access point, distal is more upstream and proximal is more downstream.

According to one aspect, the occlusive material may be a metal fabric including a plurality of strands, wherein at least one strand may be a metal strand, such as two sets of essentially parallel generally helical strands, with the strands of one set having a "hand", i.e., a direction of rotation, opposite that of the other set. The strands may be braided, interwoven, or otherwise combined to define a generally tubular fabric. The pitch of the strands (i.e., the angle defined between the turns of the strands and the axis of the braid) and the pick of the fabric (i.e., the number of wire strand crossovers per unit length) may be adjusted as desired for a particular application. The at least one wire strand of the metal fabric used in aspect of the present disclosure may be formed of a material that is both resilient and can be heat treated to substantially set a desired shape. One factor in choosing a suitable material for the at least one wire strand is that the wire(s) retain a suitable amount of the deformation induced by the molding surface (as described herein) when subjected to a predetermined heat treatment and elastically return to said molded shape after substantial deformation.

FIGS. 1 and 2 are schematics of an exemplary occlusion device 100 according to one aspect of the present disclosure. In such an aspect, the occlusion device 100 may be adapted to be received within and to occlude a cavity 200 defined by a body 225, wherein the body 225 comprises tissue forming a rim portion 250 defining an opening 275 extending into the cavity 200 and having a circumference. Such a cavity 200 may comprise, for example, the left atrial appendage (LAA) of the heart. In some instances, the occlusion device 100 may comprise first and second laterally-expandable portions 300, 400, wherein each portion may be formed of at least one metal strand woven or braided into at least one layer of a tubular fabric, and a connective element 500 extending therebetween and tethering the first and second portions 300, 400 together. In so being formed, such first and second laterally-expandable portions 300, 400 may each include opposed proximal ends 300A, 400A, and distal ends 300B, 400B, respectively. One skilled in the art will appreciate, however, that even though the disclosure herein references an occlusion device comprising first and second portions, and a connective element therebetween, such a configuration is for exemplary purposes only and that an occlusion device according to other aspects of the disclosure may comprise three or more separate and discrete portions configured to be cooperable according to the various principles herein disclosed.

Both the first and second portions 300, 400 may be configured to be insertable into the cavity 200 through the opening 275. Further, in some instances, as shown, for example, in FIG. 2, at least the first portion 300 is configured to minimally outwardly-extend from the cavity 200 past the rim portion 250, either laterally and/or longitudinally, upon lateral expansion of the first portion 300. That is, the occlusion device 100, or at least the first portion 300 thereof, may be configured so as to be substantially disposed within the cavity 200 upon lateral expansion thereof, and/or when the first portion 300 is laterally extended to engage the tissue defining the wall of the cavity 200, the proximal end 300A of the first portion 300 may be substantially flush with or juxtaposed with the rim portion 250 defining the opening 275. A connective element 500 may be operably engaged with and configured to tether the distal end 300B of the first portion 300 to the second portion 400. In some instances, the connective element 500 may be configured to tether the distal end 300B of the first portion 300 with the proximal end 400A of the second portion 400. The engagement between the connective element 500 and the respective first and second portions 300, 400 may be configured such that each of the first and second portions 300, 400 is articulable, rotatable, flexible, or otherwise movable with respect to the connective element 500. In cooperation, the first and second portion 300, 400, and the connective element 500, may be configured to form an axially and/or radially collapsible assembly (occlusion device 100) extending along an insertion axis 600 (otherwise referred to herein as a longitudinal device axis, defined by the exemplary occlusion device 100 assembly, including the first and second portions 300, 400 and the connective element 500). Further, each of the first and second portions 300, 400 may define a respective longitudinal axis 300C, 400C. In such instances, the occlusion device 100 assembly may be further configured to be insertable into the cavity 200, along the insertion axis 600, with the second portion 400 first inserted into the cavity 200, followed by the connective element 500, and then the first portion 300.

Once inserted into the cavity 200, the occlusion device 100 may be deployed and retained therein by a plurality of retention members 700 operably engaged with at least one of the first portion 300 and the second portion 400. In some instances, the retention members 700 may be operably engaged with each of the first and second portions 300, 400. In such instances, as will be appreciated by one skilled in the art, the retention members engaged with the first portion 300 may not necessarily be the same as the retention members engaged with the second portion 400 (i.e., one set of the retention members may be configured to be more robust to engage a smoother cavity surface, while the other set or retention members may be configured to be relatively less robust to engage a rougher cavity surface). According to some aspects, the retention members 700 are adapted to engage the body 225, after insertion of the collapsible assembly 100, in a collapsed state and with the second portion inserted first, into the cavity 200 along the insertion axis 600, and upon subsequent lateral expansion of the corresponding first and/or second portions 300, 400 having the retention members 700 operably engaged therewith, so as to retain the assembly 100 within the cavity 200. More particularly, each retention member 700 may be configured to be non-piercing with respect to the body 225 defining the cavity 200, and to extend at an acute angle from an outer peripheral surface of the respective one of the first and second portions, 300, 400, in a direction toward the proximal end thereof, so as to provide the securement of the first and/or second portions 300, 400 within the cavity 200. In some instances, the retention members 700 may be disposed in a spaced-apart manner about an outer circumference of the first and/or second portions 300, 400. In some aspects, the second portion 400, when laterally expanded, has a lateral dimension no greater than the maximum lateral dimension of the first portion 300, when laterally expanded.

In some aspects, the first portion 300, the second portion 400, and/or the connective element 500 of the occlusion device 100 may be formed in a mesh-like or otherwise porous configuration (such as, e.g., woven, braided, or helically wound or braided, from one or more strands into at least one layer of a fabric, in some instances, from one or more metallic strands into at least one layer of a tubular fabric), such that the first portion 300, the second portion 400, and/or the connective element 500 define openings or pores extending from the exteriors thereof to respective, generally hollow, interiors. The first portion 300, the second portion 400, and/or the connective element 500 may be comprised of a material having a shape memory property and/or a superelastic property. More particularly, such a material should desirably be both resilient and capable of being formed into a desired shape. Accordingly, in instances where the first portion 300, the second portion 400, and/or the connective element 500 are comprised of at least one strand of a metallic material, the at least one metal strand may comprise an appropriate metallic material such as, for example, a stainless steel alloy, a nickel-titanium alloy, or a cobalt-chromium-nickel alloy. More particularly, some exemplary suitable materials include a cobalt-based low thermal expansion alloy such as Elgeloy™, nickel-based high temperature high-strength "superalloys" commercially available from Haynes International under the trade name Hastelloy™ nickel-based heat treatable alloys sold under the name Incoloy™ by International Nickel, and a number of different grades of stainless steel.

One particular type of suitable material which may also meet these qualifications includes shape memory alloys such as Nitinol™, an approximately stoichiometric alloy of nickel and titanium. Such alloys may tend to exhibit a temperature-induced phase change which will cause the material to have a preferred configuration, wherein such a preferred configuration may be set by heating the material above a certain transition temperature to induce the phase change in the material. That is, the material may be held/maintained in the preferred shape (i.e., by placement of the fabric in an appropriate mold representing the desired relaxed/expanded shape of the final product) during the heat treatment process. When the material is cooled to below the transition temperature and removed from the mold, the alloy will "remember" the preferred configuration maintained during the heat treatment and will tend to revert to that configuration, unless otherwise constrained from doing so. Such shape memory alloys may also exhibit high elasticity, and may sometimes be referred to as "superelastic" or "pseudoelastic." One skilled in the art will appreciate, however, that these exemplary metal alloys/materials are not intended to be limiting in any manner with respect to the configuration of the first portion 300, the second portion 400, and/or the connective element 500 of the occlusion device 100 disclosed herein.

In one example, the first portion 300, the second portion 400, and/or the connective element 500 may be formed from at least one metal strand having a diameter of between about 0.001 inches and about 0.015 inches, preferably between about 0.003 inches and about 0.0045 inches, wherein the resulting tubular fabric may comprise between about 72 and about 144 such strands. In another example, the first portion 300, the second portion 400, and/or the connective element 500 may be formed from 72 braided Nitinol™ wires or strands having a diameter ranging between about 0.002 inches and about 0.006 inches (between about 0.051 mm and about 0.154 mm), but particularly, in some instances, between about 0.003 inches and about 0.005 inches (between about 0.077 mm and about 0.128 mm). In some instances, the first portion 300, second portion 400, and/or connective element 500 may comprises more than one layer of fabric, wherein in such instances, the metal strand diameter may range from between about 0.0015 inches and about 0.0035 inches in at least one of the layers. In some aspects, the strands may have multiple diameters within the same fabric, wherein the larger diameter strands may provide structural support, while the smaller diameter strands may provide for smaller openings or pores. The number of wires/strands to be braided may range between about 4 strands and about 288 or more strands, but particularly, in some instances, between about 32 strands and about 144 strands and, more particularly, between about 72 strands and about 144 strands, depending on the particular device characteristics desired. In some instances, the first portion 300, second portion 400, and/or connective element 500 may comprises more than one layer of fabric, wherein in such instances, the number of strands forming a given layer may be the same, or different, with respect to the number of strand used to form another layer. In some aspects, the first portion 300, the second portion 400, and/or the connective element 500 may be formed from a single length or strand of the braided metal fabric, wherein the length/strand is continuous from end to end of the occlusion device 100. A pitch angle of the at least one strand in the weave, as braided, may be on the order of between about 30 degrees and about 70 degrees with respect to the longitudinal axis 300C, 400C of the respective first and/or second portion 300, 400 (with the respective portion in a laterally expanded state and, in particular instances, prior to heat treatment or heat setting thereof). One skilled in the art will appreciate, however, that various factors such as, for example, pitch angle of the at least one strand, pick count (number of strand/wire crossovers per inch of length, or other lineal measure), and/or strand/wire diameter, may be altered, as necessary or desired, to obtain appropriate device characteristics and/or the heat set shape.

The aspect of the occlusion device 100 illustrated in FIGS. 1 and 2 shows the first and second portions 300, 400 in their respective laterally- or radially-expanded (i.e., relaxed) states. That is, the first portion 300, the second portion 400, and/or the connective element 500 may be configured so as to be self-expanding, particularly in a radial direction. More particularly, in some instances, the at least one strand woven into a tubular fabric may be configured such that axial tension applied to the tubular fabric (i.e., about the ends thereof) causes the tubular fabric to experience a reduction in cross-sectional dimension (i.e., diameter). Such reduction in cross-sectional dimension, in some instances, in conjunction with axial lengthening of the tubular fabric, may also be achieved by radially compressing the tubular fabric perpendicular to the axis thereof. In some instances, the woven tubular fabric may comprise more than one layer (i.e., the tubular fabric may be folded back over itself, or multiple separate layers may be concentrically arranged and secured together).

In one particular example, each layer of the first portion 300, the second portion 400, and/or the connective element 500 may be formed as a tubular "braid" comprised of one or more individual strands of Nitinol™ wire wound helically, and crossing over itself or one another. The woven nature of the braid holds the wires of each layer together. In forming the first portion 300, the second portion 400, and/or the connective element 500 of the occlusion device 100, an appropriately-sized (lengthwise) portion of the tubular fabric may be cut from a longer section thereof. In some aspects, the first and/or second portions 300, 400 may be configured such that the maximum lateral dimension of the first and/or second portion 300, 400, when laterally expanded, is between about 1.5 and about 5 times the length along the respective axis between the proximal and distal ends thereof. When the tubular fabric is cut, the respective axial ends typically must be addressed in order to prevent the woven/braided material from unraveling. As such, in some instances, upon or prior to cutting the tubular fabric to form the first portion 300, the second portion 400, and/or the connective element 500, the opposing axial ends of each cut portion may be sealed or otherwise secured to prevent such unraveling, for example, by soldering, brazing, welding, or other process by which the severed strand(s) can be fixed together. In one example, a biocompatible cementitious organic material may be applied to an appropriate location of the longer length of the tubular fabric, before the tubular fabric is cut to form the first portion 300, the second portion 400, and/or the connective element 500. One skilled in the art will appreciate, however, that the strands about the respective ends of the first portion 300, the second portion 400, and/or the connective element 500 may be held together to prevent unraveling through many other mechanisms known or later developed in the art. For example, besides welding or the use of adhesives to secure the ends of the braided tubular fabric, mechanical or other securement devices such as clamps or connectors may also be applied so as to prevent unraveling of the respective component and/or to allow the respective one of the first portion 300, the second portion 400, and/or the connective element 500, for instance, to be connected to an adjacent component, such as a deployment tool (i.e., the vascular catheter device) and/or the connective element 500 by way of a threaded engagement. For example, an end of the tubular fabric, such as the proximal end 300A of the first portion 300, may be engaged with a securement device so as to prevent the tubular fabric from unraveling, while a threaded configuration, for example, allows the securement device to releasably engage a delivery device configured to insert the occlusion device 100 assembly into the cavity 200. One skilled in the art will appreciate, however, that many other configurations of complementary components could be used in place of threads to facilitate the releasable engagement and deployment of the occlusion device 100 such as, for example, grooves, slots, tethers, etc.

In some instances, the tubular layers of the braided Nitinol™ wire (fabric) may be concentrically arranged with respect to one another on a forming mold, and the assembly may then be heat set to hold the tubular configuration. In such instances, one relevant property of the woven tubular fabric, thus formed, may be a radial expansive force that may be exerted thereby. For example, the woven tubular fabric may be heat set to form each of the first and second portions 300, 400 with a respective laterally-expanded diameter of between about 10% and about 30% larger than the diameter about the longitudinal position within the cavity for which the first and second portions 300, 400 are intended. That is, the radial expansive force exerted by the fabric upon radial expansion thereof facilitates retention of the device or device portion, in its deployed configuration, within the cavity in which it is inserted by exerting a biasing force against the tissue defining the cavity 200. Such retention of the tubular fabric within the cavity may also be facilitated by the retention members engaged with the device or device portions and interacting with the bodily wall defining the cavity. The connective element 500, upon formation thereof, may be heat set so as to have a relatively small expanded diameter as compared to the first and/or second portions 300, 400 so as to facilitate flexibility between the respective portions 300, 400 of the occlusion device 100 and the connective element 500.

In one aspect, at least one of the woven fabrics/fabric layers may define openings in the weave that are between about 0.0015 square inches and about 0.0003 square inches, which may sufficiently/relatively small so as to substantially preclude or impede flow therethrough. It should be noted that, as used herein, the phrase "substantially preclude or impede flow" shall indicate, functionally, that blood flow may occur for a short time, preferably between about 15 minutes and about 45 minutes, but that the body's clotting mechanism or the presence of protein or other deposits on the braided fabric, may result in occlusion or flow stoppage through the fabric after the initial period. This may be clinically represented, for example, by no contrast flow through the fabric after the 15-45 minute period as viewed by a fluoroscopy procedure after a contrast injection.

In some instances, the deployed fabric may endothelialize within the cavity and become incorporated into the bodily wall defining the cavity. In order to further encourage occlusion and thrombosis, and thereafter endothelialization, the woven tubular fabric may have at least one occluding fiber associated therewith. The at least one occluding fiber may be, for example, woven into a tubular fabric so as to form one concentric layer with the first and/or second portions 300, 400. In another example, the at least one occluding fiber may be woven into the first and/or second portion 300, 400. In yet another example, a polymer fabric may be secured, for example, by suturing, to the braided metal fabric. In various aspects, the at least one occluding fiber may be woven with the at least one metal strand, may be a fabric attached to the at least one layer of the tubular fabric, and/or may be a discrete woven tubular fabric concentrically-disposed with respect to the at least one layer of the tubular fabric.

In order to facilitate insertion thereof into the cavity 200, the occlusion device 100 may be altered from the laterally-expanded preset configuration into an axially-elongated, reduced lateral dimension configuration. For example, the first and second portions 300, 400 of the occlusion device 100 may be inserted into a vascular catheter in the axially-elongated, reduced lateral dimension configuration, for vascular delivery to a treatment site, wherein the occlusion device 100 can then be deployed from the catheter to return to the expanded preset configuration of the first and/or second portions 300, 400 (and, in some instances, the flange 325, as disclosed hereinbelow) thereof, in order to form an occlusion, flow restriction or shunt in the cavity 200 defined by a body organ, such as the LAA, or other vessel. To form a flow restrictor or shunt, an axial flow path through the fabric and/or the device or device portions may be sized and shaped, for example, by a heat set molding process similar to or simultaneously with the process used to form the first portion 300, the second portion 400, and/or the connective element 500, as previously disclosed. In one aspect, the occlusion device 100 may be configured to be insertable into the cavity 200 through the opening 275 so as to not extend, laterally or longitudinally, from the cavity 200, past the rim portion 250 thereof, upon lateral expansion of at least the first portion 300 and securement thereof in the cavity 200. That is, the occlusion device 100 may be configured such that, upon deployment, the occlusion device 100, or at least the first portion 300 thereof, may be substantially disposed within the cavity 200 and/or such that the proximal end 300A of the first portion 300 is juxtaposed with the rim portion 250 of the cavity 200.

In other aspects, as shown in FIGS. 3A and 3B, at least the first portion 300 of the occlusion device 100 may include a flange 325 operably engaged or integrally formed therewith. In some instances, the flange 325 may be configured to be articulable with respect to the first portion 300. In some particular instances, such a flange 325 may be engaged or integrally formed with the proximal end 300A of the first portion 300. The first portion 300 has a lateral dimension (i.e., width) measured transverse to and through the longitudinal axis 300C thereof. If the desired expanded preset configuration of the first portion 300 is tubular with a circular cross-section, the lateral dimension between the proximate and distal ends 300A, 300B thereof may be substantially constant. In some aspects, the first and/or second portions 300, 400 may have a substantially circular laterally-expanded cross-section. In other instances, the lateral dimension of the first and/or second portions 300, 400 may vary, as necessary or desired, between the respective proximal and distal ends, whether in cross-sectional shape or profile shape. For example, the tubular first and/or second portions 300, 400 may be configured with square-, elliptical-, oval-, hexagonal-, or any other suitable polygonal-shaped cross-section. In one instance, as shown in FIGS. 3A and 3B, the flange 325 may have an oval configuration. In some instances, a flange connective element 350 may be configured to tether the flange 325 to the first portion 300, for example, similarly to the manner in which the connective element 500 tethers the first portion 300 to the second portion 400. The flange 325 and/or the flange connective element 350 may be formed of at least one metal strand formed into at least one layer of a woven fabric. The flange 325 may have a relaxed expanded preset shape extending laterally outward past the rim portion 250 in such a manner as to overlap the circumference of the rim portion 250, in total, for less than one of one-half of the circumference of the rim portion 250, one-third of the circumference of the rim portion 250, and one-fourth of the circumference of the rim portion 250. The flange 325 may be configured to minimally engage the tissue forming the rim portion 250 and thus function as a stop or locator to facilitate proper positioning of the occlusion device 100 longitudinally/axially relative to the opening 275 of the cavity 200. In a similar manner to the connective element 500, the flange connective element 350 may likewise be heat set to a relatively small diameter in relation to the diameter of the first portion 300 so as to, for example, facilitate flexibility between the flange 325 and the first portion 300. The flange 325 and flange connective element 350 may be formed of the same fabric as the first and/or second portions 300, 400 and/or the connective element 500, wherein such a single fabric may, in some instances, extend from a proximal end of the occlusion device 100 to the distal end of the occlusion device 100. That is, in some aspects, the first and second portions 300, 400 and the connective element 500 may be formed from at least one contiguous layer of the tubular fabric. In other aspects, the first and second portions 300, 400, the connective element 500, the flange 325, and the flange connective element 350 may be formed from at least one contiguous layer of the tubular fabric.

As shown in FIG. 5, the flange 325 engaged with the proximal end 300A of the first portion 300, in some aspects via a flange connective element 350, may facilitate or otherwise allow the first portion 300 to be inserted further into the cavity 200, if necessary or desired. In some instances, the flange 325 may be configured to have at least one lateral dimension greater than a lateral dimension of the opening 275 defined by the rim portion 250, even in instances where the engagement between the first portion 300 and the body 225 defining the cavity 200 causes the opening 275 to laterally expand. In such instances, in accordance with some aspects of the present disclosure, the flange 325 may also be configured so as to not completely cover the opening 275, to minimally engage the tissue forming the rim portion 250, or otherwise be configured to have an interference relationship with respect to the tissue forming the rim portion 250. That is, the flange 325 may extend perpendicularly to the longitudinal axis 300C of the first portion 300, past the maximum lateral dimension thereof when radially expanded, such that at least a portion thereof laterally extends to a dimension greater than the lateral dimension of the rim portion 250 defining the opening 275. The flange 325 may thus be configured to engage the rim portion 250, but preferable does so without completely overlapping the opening 275 (i.e., overlapping or otherwise interfering with the circumference of the rim portion 250, in total, for less than one of one-half of the circumference of the rim portion 250, one-third of the circumference of the rim portion 250, and one-fourth of the circumference of the rim portion 250). For example, in some aspects, the flange 325 may be configured or otherwise shaped as an oval, whereby the major dimension of the oval extends to a dimension greater than the lateral dimension of the opening 275, and the minor dimension of the oval is less than the lateral dimension of the opening 275. Accordingly, when viewed along the insertion axis 600, the flange 325 will overlap the circumference of the rim portion 250 by a relatively small portion of the circumference thereof, thus forming a minimal engagement with the tissue forming the rim portion 250.

One skilled in the art will appreciate, however, that the flange 325 may be configured in many different manners so as to extend laterally or overlap only a relatively small portion of the tissue forming the rim portion 250 defining the opening 275, when the occlusion device 100 is deployed. For example, the flange 325 may be configured to be shaped as a "cross" of two intersecting elongate members. In some instances, the flange 325 associated with the first portion 300 may prevent the occlusion device 100 from being inserted/deployed too deeply in the cavity 200, or otherwise to cause the flange 325 and/or proximal end 300A of the first portion 300 to be substantially flush or otherwise juxtaposed with the tissue forming the rim portion 250 defining the opening 275. In other instances, the flange 325 may be configured not to entirely cover the opening 275. In any instances, aspects of the occlusion device 100 disclosed herein may allow other treatments/therapies to be subsequently applied to or about the affected body 225, without requiring the deployed occlusion device to be first removed (where such subsequent treatment/therapy may be otherwise precluded by a deployed occlusion device 100 having a flange covering the entire opening or otherwise overlapping a major portion of the rim portion 250). Such a subsequent treatment/therapy may be, for example, ablation therapy, wherein at least some of the rim portion 250 may be ablated to treat the atrial fibrillation condition. One skilled in the art will thus appreciate that the "flangeless" aspect of the occlusion device 100, or the "minimally-engaging" flange aspect, previously disclosed may also facilitate such subsequent treatments/therapies.

In some aspects, the flange may comprise a plurality of flange members 330 (see, e.g., FIGS. 4A and 4B), each extending laterally from the proximal end 300A of the first portion 300 and spaced apart thereabout. In such instances, the plurality of flange members 330 may be integrally formed with the first portion 300 or may otherwise be attached thereto. Further the plurality of flange members 330 may also be configured such that at least two of the flange members 330 cooperate to have a lateral dimension greater than a lateral dimension of the opening 275 defined by the rim portion 250. The flange members 330 may also be configured to cooperate to overlap the circumference of the rim portion 250, in total, for less than one of one-half of the circumference of the rim portion 250, one-third of the circumference of the rim portion 250, and one-fourth of the circumference of the rim portion 250. Similarly to the single flange 325, the plurality of flange members 330 may be configured to facilitate longitudinal/axial placement of the occlusion device 100 within the cavity 200, such that the proximal end 300A of the first portion 300 is nearly flush with the rim portion 250 and/or juxtaposed therewith, and the occlusion device 100 is substantially disposed within the cavity 200. In this regard, one skilled in the art will appreciate that the size, shape and number of flange members 330 may be varied as necessary or desired.

According to another aspect of the present disclosure, the occlusion device 100 may also be configured to be laterally and/or axially collapsible so as to facilitate insertion thereof into the cavity 200 and/or subsequent deployment. In such instances, the first portion 300, the second portion 400, and/or the connective element(s) 350, 500 may be configured to facilitate such lateral collapsibility. For example, the first portion 300, the second portion 400, and/or the connective element(s) 350, 500 may be braided such that an axial tension force applied thereto causes the first portion 300, the second portion 400, and/or the connective element(s) 350, 500 to radially or laterally contract. In other aspects, the first portion 300, the second portion 400, and/or the connective element(s) 350, 500 may be configured to facilitate an enhanced securing force (i.e., a laterally-outward biasing force for facilitating engagement between the retention element(s) 700 and the body 225 defining the cavity 200) and/or flexibility or articulability between the flange 325, the first portion 300, the second portion 400, and/or the connective element(s) 350, 500. For example, at least the distal end 300B of the first portion 300 and/or at least the proximal end 400A of the second portion 400 may be configured to be concave (see, e.g., FIG. 5), wherein such concavities may be configured to receive at least a portion of the connective element 500, so as to facilitate flexibility and/or articulation between the various components of the occlusion device 100 assembly (i.e., in the lateral (radial) and/or longitudinal (axial) direction). In this regard, the connective element 500 may be configured to have a lateral dimension smaller than the lateral dimension of the first and second portions 300, 400. The connective element 500 may also have a length of less than the length of the first and/or second portions 300, 400, and may also be configured to have a length to lateral dimension ratio of between about 2 and about 30. Further, the connective element 500 may be configured such that a ratio of the maximum lateral dimension of each of the first and second portions, 300, 400, when laterally expanded, to the lateral dimension of the connective element 500, is between about 5 and about 30. In addition, each of the first and second portions 300, 400 may be articulable, rotatable, or otherwise movable with respect to the connective element 500, and the connective element 500 may also be configured to be flexible. One skilled in the art will also appreciate that the proximal end 300A of the first portion 300 and/or the distal end 400B of the second portion 400 may also be configured to be concave so as to, for instance, receive the respective securement device(s) securing these ends of the first and second portions 300, 400, and/or securing the flange 325 to the first portion 300. In addition, the flange 325 and/or the proximal end 300A of the first portion 300 may be appropriately configured so as to be substantially flush and/or juxtaposed with the rim portion when the occlusion device 100 is deployed. In addition, the proximal and/or distal ends of the first and second portions 300, 400 may be configured in many different manners such as, for example, substantially planar, convex, concave, etc.

Method aspects of the present disclosure may advantageously involve deployment of the occlusion device 100 in a left atrial appendage of a heart, particularly a human heart. When deployed, it may be preferred that the distal end 400B of the second portion 400 of the occlusion device 100 faces an interior or end of the left atrial appendage and that the proximal end 400A faces the distal end 300B of the first portion 300, as well as the opening 275 into the left atrial appendage, while the proximal end 300A of the first portion 300 faces away from the second portion 400 toward the opening 275. If the first portion 300 does not include a flange 325, the occlusion device 100 is preferably inserted into the left atrial appendage such that the proximal end 300A of the first portion 300 is substantially disposed within the cavity 200 and flush and/or juxtaposed with the rim portion 250, or otherwise such that the first portion 300 minimally extends therefrom, laterally and/or longitudinally, past the rim portion 250, upon expansion and securement thereof by the retention devices 700 within the LAA.

In some instances, the occlusion device 100 may be connected to or otherwise engaged with a delivery device (not shown), for example, by way of a threaded connection therebetween. The delivery device may be an elongated member extending from the occlusion device 100 to a location outside the body for axial position control of the occlusion device 100 maintained in a collapsed state within a delivery catheter lumen. As such, in some instances, if a misplacement of the occlusion device 100 may occur during deployment, it may be possible for the occlusion device 100 to be withdrawn by the delivery device into the delivery catheter lumen and re-positioned, as necessary, prior to re-deployment. If the occlusion device 100 does include a flange 325 or flange members 330 associated with the first portion 300, the occlusion device 100 is preferably inserted into the left atrial appendage such that the flange 325 or flange members 330 minimally overlap the rim portion 250, without entirely covering the circumference thereof, upon expansion and securement of the occlusion device 100 by the retention devices within the LAA. Once the occlusion device 100 has been deployed, properly positioned, and secured, the delivery device may be removed, for example, by undoing the threaded connection therebetween. In any instance, one skilled in the art will appreciate that the disclosed deployment of an occlusion device within a left atrial appendage is exemplary in nature only and that aspects of the occlusion device of the present disclosure may be used in any opening, vessel, cavity, etc. of a body where occlusion is desired.

Many modifications and other aspects of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An occlusion device adapted to be received within and to occlude a cavity defined by a body, the body comprising tissue forming a rim having a circumference and defining an opening extending into the cavity, said occlusion device comprising:
    a first laterally-expandable portion formed of at least one metal strand woven into at least one layer of a tubular fabric, and having opposed proximal and distal ends, the first portion being configured to be insertable into the cavity through the opening so as to be substantially disposed within the cavity upon lateral expansion thereof;
    a second laterally-expandable portion formed of at least one metal strand woven into at least one layer of a tubular fabric, the second portion having opposed proximal and distal ends and being configured to be insertable into the cavity distally to the first portion;
    a laterally-expandable connective element formed of at least one metal strand woven into at least one layer of a tubular fabric, the connective element being operably engaged with and tethering the distal end of the first portion to the second portion, and cooperable therewith to form a collapsible assembly extending along an insertion axis, wherein at least one of the distal end of the first portion and the proximal end of the second portion defines a concavity configured to receive at least a portion of the connective element; and
    a plurality of retention members operably engaged with at least one of the first and second portions and spaced apart about a laterally outward surface thereof, the retention members configured to be non-piercing with respect to the body defining the cavity and -adapted to engage the body, upon insertion of the collapsible assembly, in a collapsed state and with the second portion first inserted distally to the first portion, into the cavity along the insertion axis and subsequent lateral expansion of the first and second portions, so as to retain the assembly substantially within the cavity.

2. The device according to claim 1, wherein the first portion is configured to be insertable into the cavity through the opening such that the proximal end thereof is juxtaposed with the rim upon lateral expansion of the first portion.

3. The device according to claim 1, wherein the connective element is configured to have a lateral dimension smaller than a lateral dimension of the first and second portions.

4. The device according to claim 1, wherein the first and second portions are configured to be articulable with respect to the connective element.

5. The device according to claim 1, further comprising a securement device operably engaged with the proximal end of the first portion, the securement device being configured to engage the at least one metal strand so as to one of prevent the tubular fabric from unraveling, and releasably engage a delivery device configured to insert the assembly through a delivery catheter into the cavity.

6. The device according to claim 1, wherein at least one of the first and second portions is comprised of a material having one of a shape memory property and a superelastic property.

7. The device according to claim 1, wherein the at least one metal strand comprises a material selected from the group consisting of a stainless steel alloy, a nickel-titanium alloy, and a cobalt-chromium-nickel alloy.

8. The device according to claim 1, wherein each retention member extends at an acute angle from the respective one of the first and second portions, toward the proximal end thereof.

9. The device according to claim 1, wherein at least one of the first and second portions comprises an occluding fiber engaged therewith.

10. The device according to claim 1, wherein the concavity is configured to receive at least a portion of the connective element, so as to facilitate at least one of flexibility between the first and second portions and biasing the plurality of retention members into engagement with the body.

11. The device according to claim 1, wherein at least one of the first and second portions is configured to be substantially cylindrical when laterally expanded.

12. The device according to claim 1, wherein the second portion, when laterally expanded, has a lateral dimension less than a lateral dimension of the first portion, when laterally expanded.

13. The device according to claim 1, wherein a maximum lateral dimension of one of the first and second portions, when laterally expanded, is between about 1.5 and about 15 times a length between the proximal and distal ends thereof.

14. The device according to claim 1, wherein a length of the connective element is less than a length of one of the first and second portions.

15. The device according to claim 1, wherein the assembly is configured to be insertable into a left atrial appendage of a heart.

16. The device according to claim 1, wherein one of the first and second portions is comprised of a plurality of layers of the tubular fabric.

17. The device according to claim 1, wherein the first and second portions and the connective element are formed from at least one contiguous layer of the tubular fabric.

18. The device according to claim 1, wherein the at least one metal strand has a diameter of between about 0.002 inches and about 0.005 inches, and the tubular fabric comprises between about 36 and about 144 strands.

19. An occlusion device adapted to be received within and to occlude a cavity defined by a body, the body comprising tissue forming a rim having a circumference and defining an opening extending into the cavity, said occlusion device comprising:
    a first laterally-expandable portion formed of at least one metal strand woven into at least one layer of a tubular fabric, and having opposed proximal and distal ends, the first portion being configured to be insertable into the cavity through the opening so as to be substantially disposed within the cavity upon lateral expansion thereof;
    a second laterally-expandable portion formed of at least one metal strand woven into at least one layer of a tubular fabric, the second portion having opposed proximal and distal ends and being configured to be insertable into the cavity distally to the first portion; and
    a laterally-expandable connective element having a length to lateral dimension ratio of between about 2 and about 30 and formed of at least one metal strand woven into at least one layer of a tubular fabric, the connective element being operably engaged with and tethering the distal end of the first portion to the second portion, and cooperable therewith to form a collapsible assembly extending along an insertion axis.

20. An occlusion device adapted to be received within and to occlude a cavity defined by a body, the body comprising tissue forming a rim having a circumference and defining an opening extending into the cavity, said occlusion device comprising:

a first laterally-expandable portion formed of at least one metal strand woven into at least one layer of a tubular fabric, and having opposed proximal and distal ends, the first portion being configured to be insertable into the cavity through the opening so as to be substantially disposed within the cavity upon lateral expansion thereof;

a second laterally-expandable portion formed of at least one metal strand woven into at least one layer of a tubular fabric, the second portion having opposed proximal and distal ends and being configured to be insertable into the cavity distally to the first portion; and a laterally-expandable connective element formed of at least one metal strand woven into at least one layer of a tubular fabric, the connective element being operably engaged with and tethering the distal end of the first portion to the second portion, and cooperable therewith to form a collapsible assembly extending along an insertion axis, wherein the ratio of a maximum lateral dimension of each of the first and second portions, when laterally expanded, to a lateral dimension of the connective element is between about 5 and about 30.

* * * * *